US006335009B1

(12) United States Patent
Bürkle et al.

(10) Patent No.: US 6,335,009 B1
(45) Date of Patent: *Jan. 1, 2002

(54) VECTORS AND VIRUSES FOR USE IN GENE THERAPY

(75) Inventors: Alexander Bürkle, Leimen; Harald Zur Hausen, Waldmichlbach; Küpper Jan-Heiner, Mauer, all of (DE)

(73) Assignee: Deutsches Krebsforschungszentrum Stiftung des Offentlichen Rechts, Heidelberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,886

(22) PCT Filed: Dec. 15, 1995

(86) PCT No.: PCT/DE95/01817

§ 371 Date: Oct. 3, 1997

§ 102(e) Date: Oct. 3, 1997

(87) PCT Pub. No.: WO96/18737

PCT Pub. Date: Jun. 20, 1996

(30) Foreign Application Priority Data

Dec. 16, 1994 (DE) .................................... P 44 44 949

(51) Int. Cl.[7] ........................ A61K 48/00; C12N 15/88

(52) U.S. Cl. ........................ 424/93.2; 514/44; 435/320; 435/455

(58) Field of Search ............................ 435/172.3, 455, 435/458, 320.1, 325, 69.1; 424/93.2, 93.21; 514/44; 536/23.1

(56) References Cited

U.S. PATENT DOCUMENTS 5,449,605 A * 9/1995 Smulson et al. ............... 435/6
5,585,254 A * 12/1996 Maxwell et al. ............ 435/455

FOREIGN PATENT DOCUMENTS

EP 0 293 193 11/1988

OTHER PUBLICATIONS

Weatherall D. (British Med. Bulletin 1995, vol. 51, No. 1, pp. 1–11).*

Mastrangelo et al. (Seminars in Oncology, vol. 23, 1996, pp. 4–21).*

Kupper et al. (J. Biological Chemistry. vol. 265, 1990, pp. 18721–18724).*

Jolly D. (Cancer Gene Therapy, vol. 1, No. 1, 1994, pp. 51–64).*

Sakamoto et al. (J. Antibiotics, (1983 Mar) 36 (3) 296–300).*

Ngo et al. (in The Protein Folding Problem and Tertiary Structure Prediction, Merz et al., (ed.), Birkhauser, Boston, MA, pp. 492–495), 1994.*

Meng et al. (Gene Therapy of Cancer, Chapter 1, pp. 3–20), 1999.*

Anderson, Nature, vol. 392, pp. 25–30, 1998.*

Astell et al., 1986, "DNA Sequence of the Lymphotropic Variant of Minute Virus of Mice, MVM(i), and Comparison with the DNA Sequence of the Fibrotropic Prototype Strain," *J. Virol.* 57(2):656–669.

Auer et al., 1989, "Human Nuclear NAD$^+$ ADP–Ribosyltransferase(polymerizing): Organization of the Gene," *DNA* 8(8):575–580.

Belt et al., 1989, "Constuction and Properties of an Epstein-Barr–Virus–Derived cDNA Expression Vector for Human Cells," *Gene* 84:407–417.

Kang et al., 1992, "Strategies for Expressing Analogs of PADPRP in Eukaryotic Cells," *ADP–Ribosylation React.* 72–6.

Keller et al., 1985, "Expression of a Foreign Gene in Myeloid and Lymphoid Cells Derived from Multipotent Haematopoietic Precursors," *Nature* 318(14):149–154.

Küpper et al., 1990, "Inhibition of Poly(ADP–ribosyl)ation by Overexpressing the Poly(ADP–ribose) Polymerase DNA–binding Domain in Mammalian Cells," *J. Biol. Chem.* 265(31):18721–18724.

Russell et al., 1992, "Transformation–Dependent Expression of Interleukin Genes Delivered by a Recombinant Parvovirus," *J. Virol.* 66(5):2821–2828.

Samulski et al., 1987, "A Recombinant Plasmid from Which an Infectious Adeno–Associated Virus Genome Can be Excised In Vitro and Its Use to Study Viral Replication," *J. Virol.* 61(10):3096–3101.

* cited by examiner

*Primary Examiner*—Dave T. Nguyen
(74) *Attorney, Agent, or Firm*—Pennie & Edmonds LLP

(57) ABSTRACT

The present invention relates to a vector suitable for use in gene therapy, which comprises an expressible insert DNA which codes for the DNA binding domain of a poly(ADP-ribose)-polymerase or for an at least partially catalytically inactive poly(ADP-ribose)-polymerase. Furthermore, this invention concerns processes for the preparation of such a vector and viruses suitable for use in gene therapy.

2 Claims, 4 Drawing Sheets

FIG. 1A

```
                                                                                              ↓-29
5'-----------------------TGCGGCTGGGTGAGCGCACGCGAGGCGGCGAGGCGGCAGCGTGTTTCTAGGTCGTGGCGTCGGGCTTCCGGAGCTTTGGCGGCAGCTAGGGGAGG   -1

1                  10                  20                  30                  40                  50
MetAlaGluSerSerAspLysLeuTyrArgValGluTyrAlaLysSerGluArgAlaSerCysLysLysCysSerGluSerIleProLysAspSerLeuArgMetAlaIleMetValGlnSerProMetPheAspGlyLysValProHis
ATGGCGGAGTCTTCGGATAAGCTCTATCGAGTCGAGTACGCCAAGAGCGAGCGCGCCTCTTGCAAGAAATGCAGCGAGAGCATCCCCAAGGACTCGCTCCGGATGGCCATCATGGTGCAGTCGCCCATGTTTGATGGAAAAGTCCCACAC   150

                   60                  70                  80                  90                  100
TrpTyrHisPheSerCysPheTrpLysValGlyHisSerIleArgHisProAspValGluValAspGlyPheSerGluLeuArgTrpAspAspGlnGlnLysValLysLysThrAlaGluAlaGlyGlyValThrGlyLysGlyGlnAsp
TGGTACCACTTCTCCTGCTTCTGGAAGGTGGGCCACTCCATCCGGCACCCTGACGTTGAGGTGGATGGGTTCTCTGAGCTTCGGTGGGATGACCAGCAGAAAGTCAAGAAGACAGCGGAAGCTGGAGGAGTGACAGGCAAAGGCCAGGAT   300

                   110                 120                 130                 140                 150
GlyIleGlySerLysAlaGluLysThrLeuGlyAspPheAlaAlaGluTyrAlaLysSerAsnArgSerThrCysLysGlyCysMetGluLysIleGluLysGlyGlnValArgLeuSerLysLysMetValAspProGluLysProGln
GGAATTGGTAGCAAGGCAGAGAAGACTCTGGGTGACTTTGCAGCAGAGTATGCCAAGTCCAACAGAAGTACGTGCAAGGGGTGTATGGAGAAGATAGAAAAGGGCCAGGTGCGCCTGTCCAAGAAGATGGTGGACCCGGAGAAGCCACAG   450

                   160                 170                 180                 190                 200
LeuGlyMetIleAspArgTrpTyrHisProGlyCysPheValLysAsnArgGluGluLeuGlyPheArgProGluTyrSerAlaSerGlnLeuLysGlyPheSerLeuLeuAlaThrGluAspLysGluAlaLeuLysLysGlnLeuPro
CTAGGCATGATTGACCGCTGGTACCATCCAGGCTGCTTTGTCAAGAACAGGGAGGAGCTGGGTTTCCGGCCCGAGTACAGTGCGAGTCAGCTCAAGGGCTTCAGCCTCCTTGCTACAGAGGATAAAGAAGCCCTGAAGAAGCAGCTCCCA   600

                   210                 220                 230                 240                 250
GlyValLysSerGluGlyLysArgLysGlyAspLysValAspGlyValAspGluValAlaLysLysLysSerLysLysGluLysAspLysAspSerLysLeuGluLysArgLeuLysAlaGlnAsnAspLeuIleTrpAsnIleLysAsp
GGAGTCAAGAGTGAAGGAAAGAGAAAAGGCGATAAGGTGGATGGAGTGGATGAAGTGGCGAAGAAGAAATCTAAAAAAGAAAAAGACAAGGATAGTAAGCTTGAAAAACGCCTAAAGGCTCAGAACGACCTGATCTGGAACATCAAGGAC   750

                   260                 270                 280                 290                 300
GluLeuLysLysValCysSerThrAsnAspLeuLysGluLeuLeuIlePheAsnLysGlnGlnValProSerGlyGluSerAlaIleLeuAspArgValAlaAspGlyMetValPheGlyAlaLeuLeuProCysGluGluCysSerGly
GAGCTAAAGAAAGTGTGTTCAACTAATGACCTGAAGGAGCTACTCATCTTCAACAAGCAGCAAGTGCCTTCTGGGGAGTCGGCGATCTTGGACCGAGTAGCTGATGGCATGGTGTTCGGTGCCCTCCTTCCCTGCGAGGAATGCTCGGGT   900

                   310                 320                 330                 340                 350
GlnLeuValPheLysSerAspAlaTyrTyrCysThrGlyAspValThrAlaTrpThrLysCysMetValLysThrGlnThrProAsnArgLysGluTrpValThrProLysGluPheArgGluIleSerTyrLeuLysLysLeuLysVal
CAGCTGGTCTTCAAGAGCGATGCCTATTACTGCACTGGGGACGTCACTGCCTGGACCAAGTGTATGGTCAAGACACAGACACCCAACCGGAAGGAGTGGGTAACCCCAAAGGAATTCCGAGAAATCTCTTACCTCAAGAAATTGAAGGTT   1050

                   360    ▼            370    ▼    ▼ ↓+1127    380    ▼          390                 400
LysLysGlnAspArgIlePheProProGluThrSerAlaSerValAlaHisProProProSerThrAlaSerAlaProAlaAlaValAsnSerSerAlaSerAlaAspLysProLeuSerAsnMetLysIleLeuThrLeuGlyLysLeu
AAAAAGCAGGACCGTATATTCCCCCCAGAAACCAGCGCCTCCGTGGCCCACCCTCCGCCCTCCACAGCCTCGGCTCCTGCTGCTGTGAACTCCTCTGCTTCAGCAGATAAGCCATTATCCAACATGAAGATCCTGACTCTCGGGAAGCTG   1200

                   410                 420                 430                 440                 450
SerArgAsnLysAspGluValLysAlaMetIleGluLysLeuGlyGlyLysLeuThrGlyThrAlaAsnLysAlaSerLeuCysIleSerThrLysLysGluValGluLysMetAsnLysLysMetGluGluValLysGluAlaAsnIle
TCCCGGAACAAGGATGAAGTGAAGGCCATGATTGAGAAACTCGGGGGGAAGTTAACGGGGACGGCCAACAAGGCTTCCCTGTGCATCAGCACCAAAAAGGAGGTGGAAAAGATGAATAAGAAGATGGAGGAAGTAAAGGAAGCCAACATC   1350

                   460                 470                 480                 490                 500
ArgValValSerGluAspPheLeuGlnAspValSerAlaSerThrLysSerLeuGlnGluLeuPheLeuAlaHisIleLeuSerProTrpGlyAlaGluValLysAlaGluProValGluValValAlaProArgGlyLysSerGlyAla
CGAGTTGTGTCTGAGGACTTCCTCCAGGACGTCTCCGCCTCCACCAAGAGCCTTCAGGAGTTGTTCTTAGCGCACATCTTGTCCCCTTGGGGGGCAGAGGTGAAGGCAGAGCCTGTTGAAGTTGTGGCCCCCAAGAGGGAAGTCAGGGGCT   1500

                   510                 520       ▼         530                 540                 550
AlaLeuSerLysLysSerLysGlyGlnValLysGluGluGlyIleAsnLysSerGluLysArgMetLysLeuThrLeuLysGlyGlyAlaAlaValAspProAspSerGlyLeuGluHisSerAlaHisValLeuGluLysGlyGlyLys
GCGCTCTCCAAAAAAAGCAAGGGCCAGGTCAAGGAGGAAGGTATCAACAAATCTGAAAAGAGAATGAAATTAACTCTTAAAGGAGGAGCAGCTGTGGATCCTGATTCTGGACTGGAACACTCTGCGCATGTCCTGGAGAAAGGTGGGAAG   1650
```

```
                610                 620                 630                 640                 650
GluGlnMetProSerLysGluAspAlaIleGluHisPheMetLysLeuTyrGluGluLysThrGlyAsnAlaTrpHisSerLysAsnPheThrLysTyrProLysLysPheTyrProLeuGluIleAspTyrGlyGlnAspGluGluAla
GAACAGATGCCGTCCAAGGAGGATGCCATTGAGCACTTCATGAAATTATATGAAGAAAAAACCGGGAACGCTTGGCACTCCAAAAATTTCACGAAGTATCCCAAAAAGTTCTACCCCCTGGAGATTGACTATGGCCAGGATGAAGAGGCA   1950

      ▼         660                 670                 680                 690                 700
ValLysLysLeuThrValAsnProGlyThrLysSerLysLeuProLysProValGlnAspLeuIleLysMetIlePheAspValGluSerMetLysLysAlaMetValGluTyrGluIleAspLeuGlnLysMetProLeuGlyLysLeu
GTGAAGAAGCTGACAGTAAATCCTGGCACCAAGTCCAAGCTCCCCAAGCCAGTTCAGGACCTCATCAAGATGATCTTTGATGTGGAAAGTATGAAGAAAGCCATGGTGGAGTATGAGATCGACCTTCAGAAGATGCCCTTGGGGAAGCTG   2100

                710                 720                 730                 740                 750
SerLysArgGlnIleGlnAlaAlaTyrSerIleLeuSerGluValGlnGlnAlaValSerGlnGlySerSerAspSerGlnIleLeuAspLeuSerAsnArgPheTyrThrLeuIleProHisAspPheGlyMetLysLysProProLeu
AGCAAAAGGCAGATCCAGGCCGCATACTCCATCCTCAGTGAGGTCCAGCAGGCGGTGTCTCAGGGCAGCAGCGACTCTCAGATCCTGGATCTCTCAAATCGCTTTTACACCCTGATCCCCCACGACTTTGGGATGAAGAAGCCTCCGCTC   2250

                760                 770                 780                 790                 800
LeuAsnAsnAlaAspSerValGlnAlaLysValGluMetLeuAspAsnLeuLeuAspIleGluValAlaTyrSerLeuLeuArgGlyGlySerAspAspSerSerLysAspProIleAspValAsnTyrGluLysLeuLysThrAspIle
CTGAACAATGCAGACAGTGTGCAGGCCAAGGTGGAAATGCTTGACAACCTGCTGGACATCGAGGTGGCCTACAGTCTGCTCAGGGGAGGGTCTGATGATAGCAGCAAGGATCCCATCGATGTCAACTATGAGAAGCTCAAAACTGACATT   2400

                810                 820                 830                 840                 850
LysValValAspArgAspSerGluGluAlaGluIleIleArgLysTyrValLysAsnThrHisAlaThrThrHisAsnAlaTyrAspLeuGluValIleAspIlePheLysIleGluArgGluGlyGluCysGlnArgTyrLysProPhe
AAGGTGGTTGACAGAGATTCTGAAGAAGCCGAGATCATCAGGAAGTATGTTAAGAACACTCATGCAACCACACACAATGCGTATGACTTGGAAGTCATCGATATCTTTAAGATAGAGCGTGAAGGCGAATGCCAGCGTTACAAGCCCTTT   2550

                860                 870                 880                 890                 900
LysGlnLeuHisAsnArgArgLeuLeuTrpHisGlySerArgThrThrAsnPheAlaGlyIleLeuSerGlnGlyLeuArgIleAlaProProGluAlaProValThrGlyTyrMetPheGlyLysGlyIleTyrPheAlaAspMetVal
AAGCAGCTTCATAACCGAAGATTGCTGTGGCACGGGTCCAGGACCACCAACTTTGCTGGGATCCTGTCCCAGGGTCTTCGGATAGCCCCGCCTGAAGCGCCCGTGACAGGCTACATGTTTGGTAAAGGGATCTATTTCGCTGACATGGTC   2700

                910                 920                 930                 940                 950
SerLysSerAlaAsnTyrCysHisThrSerGlnGlyAspProIleGlyLeuIleLeuLeuGlyGluValAlaLeuGlyAsnMetTyrGluLeuLysHisAlaSerHisIleSerLysLeuProLysGlyLysHisSerValLysGlyLeu
TCCAAGAGTGCCAACTACTGCCATACGTCTCAGGGAGACCCAATAGGCTTAATCCTGTTGGGAGAAGTTGCCCTTGGAAACATGTATGAACTGAAGCACGCTTCACATATCAGCAAGTTACCCAAGGGCAAGCACAGTGTCAAAGGTTTG   2850

                960                 970                 980                 990                1000
GlyLysThrThrProAspProSerAlaAsnIleSerLeuAspGlyValAspValProLeuGlyThrGlyIleSerSerGlyValAsnAspThrSerLeuLeuTyrAsnGluTyrIleValTyrAspIleAlaGlnValAsnLeuLysTyr
GGCAAAACTACCCCTGATCCTTCAGCTAACATTAGTCTGGATGGTGTAGACGTTCCTCTTGGGACCGGGATTTCATCTGGTGTGAATGACACCTCTCTACTATATAACGAGTACATTGTCTATGATATTGCTCAGGTAAATCTGAAGTAT   3000

               1010
LeuLeuLysLeuLysPheAsnPheLysThrSerLeuTrp
CTGCTGAAACTGAAATTCAATTTTAAGACCTCCCTGTGGTAATTGGGAGAGGTAGCCGAGTCACACCCGGTGGCTCTGGTATGAATTCACCCGAAGCGCTTCTGCACCAACTCACCTGGCCGCTAAGTTGCTGATGGGTAGTACCTGTAC   3150

TAAACCACCTCAGAAAGGATTTTACAGAAACGTGTTAAAGGTTTTCTCTAACTTCTCAAGTCCCTTGTTTTGTGTTGTGTCTGTGGGGAGGGGTTGTTTTGGGGTTGTTTTTGTTTTTTCTTGCCAGGTAGATAAAACTGACATAGAGAA   3300

AAGGCTGGAGAGAGATTCTGTTGCATAGACTAGTCCTATGGAAAAAACCAAGCTTCGTTAGAATGTCTGCCTTACTGGTTTCCCCAGGGAAGGAAAAATACACTTCCACCCTTTTTTCTAAGTGTTCGTCTTTAGTTTTGATTTTGGAAA   3450

GATGTTAAGCATTTATTTTTAGTTAAAAATAAAAACTAATTTCATACTATTTAGATTTTCTTTTTTATCTTGCACTTATTGTCCCCTTTTTAGTTTTTTTTGTTTGCCTCTTGTGGTGAGGGGTGTGGGAAGACCAAAGGAAGGAACGCT   3600

AACAATTTCTCATACTTAGAAACAAAAAGAGCTTTCCTTCTCCAGGAATACTGAACATGGGAGCTCTTGAAATATGTAGTATTAAAAGTTGCATTTG--------------------3'
```

FIG. 1B

VECTORS AND VIRUSES FOR USE IN GENE THERAPY

This is a national phase filing of the Application No. PCT/DE95/01817, which was filed with the Patent Corporation Treaty on Dec. 15, 1995, and is entitled to priority of the German Patent Application P 44 44 949.6, filed Dec. 16, 1994.

FIELD OF THE INVENTION

The present invention relates to vectors and viruses suitable for use in gene therapy, processes for the production thereof and their use.

BACKGROUND OF THE INVENTION

Common oncotherapy comprises the surgical removal of the tumor and the patient's aftertreatment by means of irradiation and/or systemic application of cytostatic agents. By means of the aftertreatment it is tried to kill non-removed tumor tissue and metastases formed, respectively.

However, common oncotherapies show little success. In particular, side-effects such as induction of secondary tumors, damage of internal organs or pains frequently occur in aftertreated patients.

Thus, it is the object of the present invention to provide means serving for improving common oncotherapies and avoiding particularly the above side effects.

SUMMARY OF THE INVENTION

The present invention relates to a vector suitable for use in gene therapy, which comprises an expressible insert DNA which codes for the DNA binding domain of a poly(ADP-ribose)-polymerase or for an at least partially catalytically inactive poly(ADP-ribose)-polymerase. Furthermore, this invention concerns processes for the preparation of such a vector and viruses suitable for use in gene therapy.

BRIEF DESCRIPTION OF THE DRAWINGS

FIGS. 1A and 1B collectively show a DNA (SEQ. ID NO:1) encoding for the DBD of a human PARP between positions 65 and 1220 (SEQ. ID NO: 1) and its deduced amino acid sequence (SEQ ID NO:2).

DETAILED DESCRIPTION OF THE INVENTION

Figure 2:
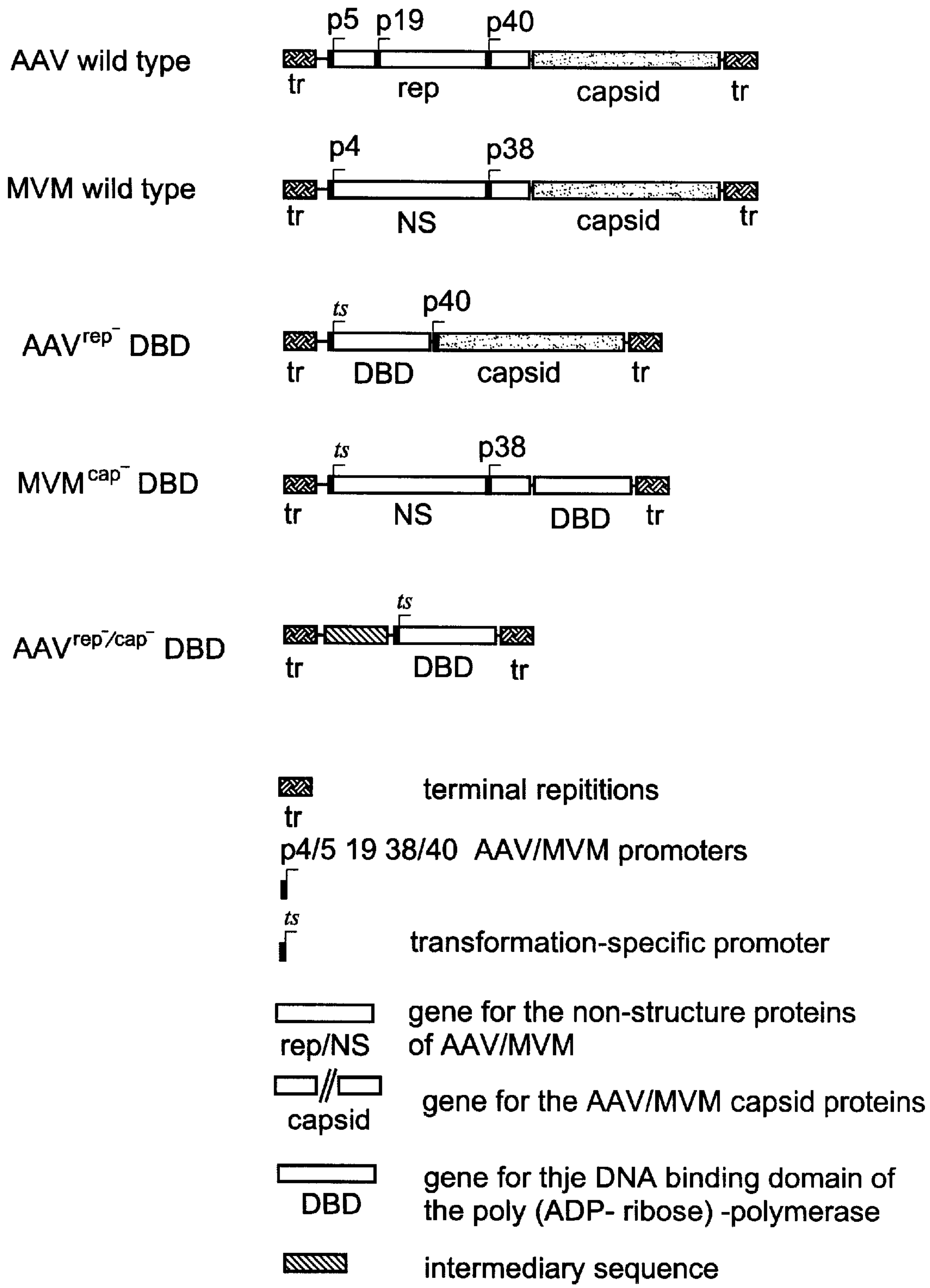
FIG. 2 shows the vectors $AAV^{rep-}$DBP, $MVM^{cap-}$DBD and $AAV^{rep-/cap-}$DBD according to the invention.

According to the invention this is achieved by a vector suitable for use in gene therapy and comprising an expressible insert DNA coding for the DNA binding domain (referred to as DBD below) of a poly(ADP-ribose)-polymerase (referred as to PARP below) or for an at least partially catalytically inactive PARP.

The present invention is based on the applicant's finding that the activity of PARP, an enzyme required for repairing DNA damage, is inhibited by the addition of DBD molecules and the repair rate of DNA damage is reduced drastically.

The above expression "vector suitable for use in gene therapy" comprises any vectors which can be used in gene therapy as such or together with other means. These are, e.g., plasmid vectors and viral vectors. Of the latter particularly those of adenovirus, herpes simplex virus, adeno-associated virus (referred to as AAV below), "minute virus of mice" (referred to as MVM below) and retroviruses are to be mentioned. Viral vectors of AAV, e.g., AAV-sub201 are to be mentioned. Viral vectors of AAV, e.g., AAV-sub201 (Samulski et al., 1987, *J. Virol.* 61:3096–3101) of MVM, e.g., pSR2 (Russell et al., 1992, *J. Virol.* 66:2821–2828) and of retroviruses, e.g., N2 (Keller et al., 1985, *Nature* 318:149–154) are especially preferred.

According to the invention an insert DNA is inserted in an above vector, which codes for the DBD of a PARP or for an at least partially catalytically inactive PARP. An above insert DNA c an originate from any organism, e.g., from man or animals or from plants. An insert DNA from man is used preferably and that of FIG. 1A and 1B, positions 65 and 1220 (SEQ ID NO: 1), or a DNA differing therefrom by one or more nucleotides is especially preferred.

The above insert DNA is inserted in the vector such that the insert DNA can be expressed. This can be achieved by inserting the insert DNA in phase in an expression unit present in the vector. For this purpose, it may be necessary to at least partially remove a DNA present in the expression unit. It may also be advantageous to replace elements of the existing expression unit such as enhancer, promoter or polyadenylation signals, at least partially by others. A promoter is preferably inserted in an expression unit, which is specific for a tissue kind, so that the expression of the insert DNA controlled by the promoter becomes tissue-specific. A promoter which is active in tumor cells is especially preferred. An example of such a promoter is the P4 promoter of MVM. Russell, et al., supra.

The expression of the above insert DNA can also be achieved in an expression unit which has to be inserted in the vector for this purpose. The above statements also apply to this expression unit.

In the case of viral vectors it often proves to be favorable to insert the insert DNA in an expression unit present in the vector. The removal or partial removal of virus DNA present in the expression unit, which is accompanied by this under certain circumstances, then results in a viral vector which has a defect in a virus function. This defect can be utilized as a selection marker. On the other hand, the defect can be compensated, if necessary, by conventional methods such as complementation in trans.

Figure 3:
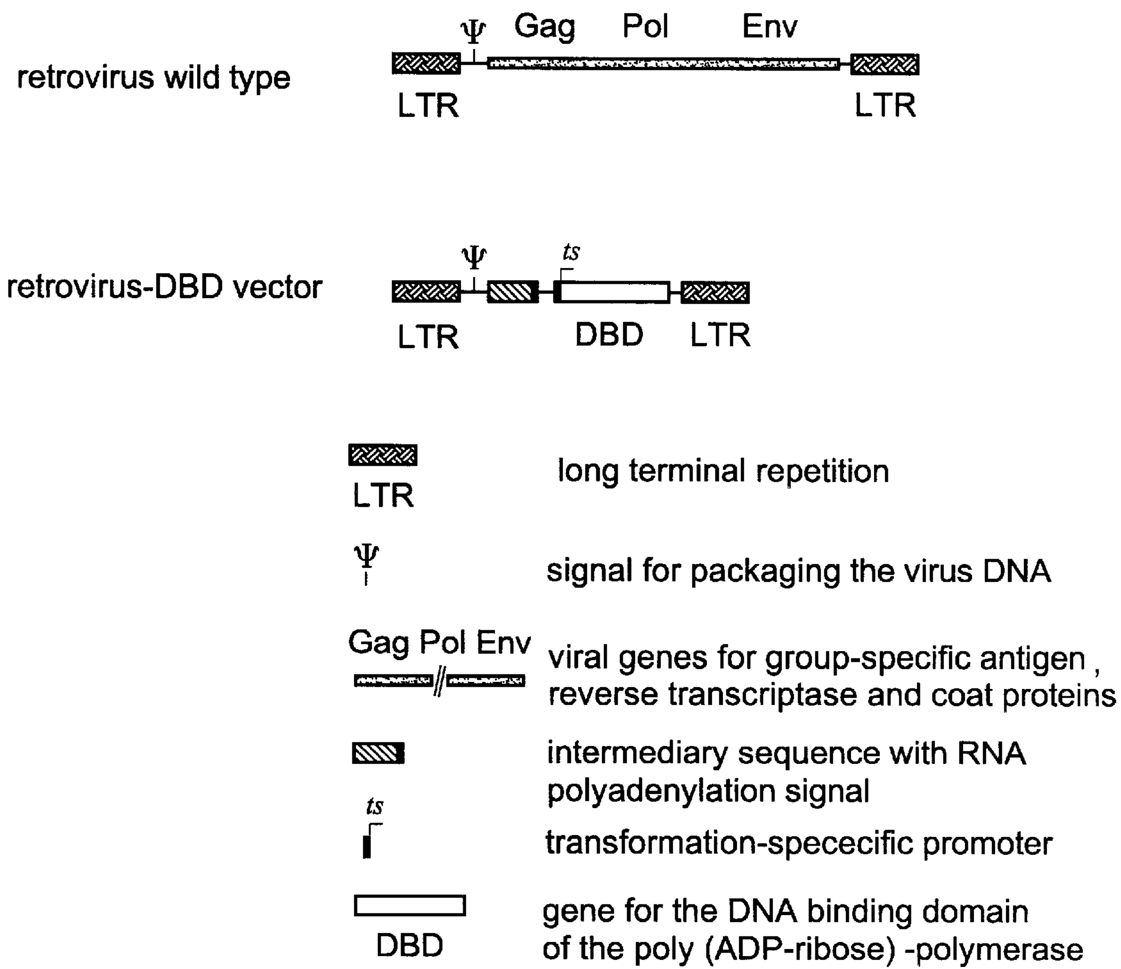
FIG. 3 shows the retrovirus DBD vector according to the invention.

According to the invention viral vectors are preferred in which the insert DNA is inserted such that the viral vectors as such are no longer capable of forming the viruses coded by them. Examples of such viral vectors are indicated in FIGS. 2 and 3. They are AAV $^{rep-}$DBD, $MVM^{cap-}$DBD and $AAV^{rep-/cap}$-DED (FIG. 2). However, the viruses coded by them can be formed by conventional complementation methods. For example, $AAV^{rep-}$DBD is transfected into cells which are simultaneously cotransfected with a DNA construct expressing the rep gene. Viruses are obtained. They are well suited for gene therapy, since they cannot multiply in patients.

Furthermore, FIG. 3 refers to the preferred retrovirus DBD vector. The virus coded by the viral vector is obtained by transfection into a conventional packaging cell line. It is also well suited for gene therapy.

Thus, the subject matter of the present invention also relates to viruses coded by the above viral vectors.

Vectors and viruses according to the invention distinguish themselves in that they can inhibit the repair of DNA damage. Therefore, they are suitable in the best possible way to be used in treatments in which cells are to be killed. The suitability of the vectors and viruses according to the invention is especially suitable for the treatment of tumors, particularly together with conventional irradiation methods and/or treatments with cytostatic agents. In this case, it is especially important that they can be tissue (tumor)-specifically active. The present invention is trend-setting for the gene-therapeutic treatment of the most serious diseases.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

A. Example 1

Preparation of the Vector AAV $^{rep-}$DBD According to the Invention

The vector AAV-sub201 (Samulski et al., supra) is used as a basis. This vector is cleaved with the restriction enzymes Xbal and BstbI. A 3.3 kb vector fragment and a 1.4 kb Rep fragment are obtained. The latter extends to the 5' end of the p40 promoter and is discarded. The ends of the vector fragment are "made blunt". An insert, P4-DBD-poly A, is inserted therein, which from 5' to 3' comprises the following sequences: (I) a 259 bp BamHI/NcoI fragment containing the P4 promoter. This fragment originates, e.g., from the plasmid pEG618 (Astell et al., 1986, *J. Virol.* 57:656–669); (II) a 1.73 kb EcoRI/HindIII fragment from pPARP6 (K üpper et al., 1990, *J. Biol. Chem.* 265:18721–18724) which includes both the 1.1 kb DBD and the 630 bp HSV thymidine kinase poly-A signal. The vector AAV $^{rep-}$DBD is obtained.

B. Example 2

Preparation of the Vector MVM $^{cap-}$DBD According to the Invention

The vector pSR2 (Russell et al., supra) is used as a basis. This vector is cleaved with HindIII and BglII. A vector fragment and a 1.6 kb capsid fragment (II) of MVM are obtained. The latter fragment is removed and replaced by the insert fragment (II) of Example 1, DBD-poly-A. The vector MVM $^{cap-}$DBD is obtained.

C. Example 3

Preparation of the Vector AAV $^{rep-cap}$ $^{-}$DBD According to the Invention

The vector AAV-sub201 of Example 1 is used as a basis. This vector is cleaved with XbaI, and all of the AAV constituents—with the exception of the terminal repetitions—are removed. The rest of the fragment is ligated with the intermediary sequence, e.g., a 2.4 kb BamHI/BamHI fragment from pCosAGy2 (Auer et al., 1989, *DNA* 8:575–580) which has non-coding sequences from the 7th intron of human PARP. Thereafter, fragments I and II of Example 1 are inserted. The vector AAV $^{rep-/cap-}$DBD is obtained.

D. Example 4

Preparation of the Retrovirus DBD Vector According to the Invention

The vector N2 (Keller et al., supra) is used as a basis. This vector is opened with EcoRI partial digest 3' of the neomycin gene. Then, the following sequences are inserted in the vector from 5' to 3' at the 3' end of the neomycin gene: (I) the 0.7 kb poly-A signal of the β-globin gene (e.g., the EcoRI/SalI fragment from pECV; Berg et al., 1989, *Gene* 4:407–417); (II) a 259 bp BamHI/NcoI fragment which contains the p4 promoter (Example 1, (I)); (III) a 1.73 kb EcoRI/HindIII fragment from pPARP6 (Example 1, (II)). The retrovirus DBD vector is obtained.

E. Example 5

Inhibition of the Repair of DNA Damage

The inhibition of the repair of DNA damage is shown by means of the inhibition of the synthesis of poly(ADP-ribose). The vector AAV$^{rep-}$DBD according to the invention is transfected into HeLa cells by means of electroporation. Following the transfection, the cells are seeded onto cover glasses for the purpose of microscopy. Two days later, the transfected cells on the cover glasses are subjected to a genotoxic treatment, e.g., x-ray therapy or treatment with alkylating cancerogens. DNA breakages result therefrom which lead to an activation of PARP which then synthesizes poly(ADP-ribose). The HeLA cells are fixed with trichloroacetic acid within 30 minutes following the genotoxic treatment and subjected to an indirect immunofluorescence against poly(ADP-ribose). No poly (ADP-ribos)-specific signals are obtained.

This shows that the DBD expressed in cells causes an inhibition of PARP.

All references cited within the body of the instant specification are hereby incorporated by reference in their entirety.

---

What is claimed is:

1. A method of enhancing the sensitivity of a tumor cell in a tumor of a cancer patient to a DNA damaging agent or irradiation comprising directly delivering to the tumor an effective amount of a tumor therapeutic, wherein said tumor therapeutic comprises a viral vector, said viral vector comprises a promoter operably linked to a poly (ADP-ribose)-polymerase encoding polynucleotide, said viral vector is an adeno-associated virus vectors a mouse-minute virus vector, or a retroviral vector, and said polynucleotide encodes a truncated or mutant poly(ADP-ribose)-polymerase that is deficient for an enzymatic activity but that has a DNA binding domain and reduces poly(ADP-ribosyl)ation catalyzed by a wild-type poly(ADP-ribose)-polymerase in a cell culture assay.

2. A method of killing a tumor cell in a tumor of a cancer patient comprising the steps of:

a) directly delivering to the tumor an effective amount of a tumor therapeutic; and b) contacting the tumor with a DNA damaging agent or irradiation, whereby the tumor cell is killed;

wherein said tumor therapeutic comprises a viral vector, said viral vector comprises a promoter operably linked to a poly(ADP-ribose)-polymerase encoding polynucleotide, said viral vector is an adeno-associated virus vector, a mouse-minute virus vector, or a retroviral vector, and said polynucleotide encodes a truncated or mutant poly(ADP-ribose)-polymerase that is deficient for an enzymatic activity but that has a DNA binding domain and reduces poly(ADP-ribosyl)ation catalyzed by a wild-type poly(ADP-ribose)-polymerase in a cell culture assay.

* * * * *

```
                        SEQUENCE LISTING


(1) GENERAL INFORMATION:

   (iii) NUMBER OF SEQUENCES: 2


(2) INFORMATION FOR SEQ ID NO:1:

     (i) SEQUENCE CHARACTERISTICS:
          (A) LENGTH: 3792 base pairs
          (B) TYPE: nucleic acid
          (C) STRANDEDNESS: single
          (D) TOPOLOGY: linear
```

-continued

```
    (ix) FEATURE:
          (A) NAME/KEY: Coding Sequence
          (B) LOCATION: 96...3134
          (D) OTHER INFORMATION:

    (xi) SEQUENCE DESCRIPTION: SEQ ID NO:1:

TGCGGCTGGG TGAGCGCACG CGAGGCGGCG AGGCGGCAGC GTGTTTCTAG GTCGTGGCGT     60

CGGGCTTCCG GAGCTTTGGC GGCAGCTAGG GGAGG ATG GCG GAG TCC TCG GAT       113
                                       Met Ala Glu Ser Ser Asp
                                        1               5

AAG CTC TAT CGA GTC GAG TAC GCC AAG AGC GAG CGC GCC TCT TGC AAG      161
Lys Leu Tyr Arg Val Glu Tyr Ala Lys Ser Glu Arg Ala Ser Cys Lys
            10                  15                  20

AAA TGC AGC GAG AGC ATC CCC AAG GAC TCG CTC CGG ATG GCC ATC ATG      209
Lys Cys Ser Glu Ser Ile Pro Lys Asp Ser Leu Arg Met Ala Ile Met
        25                  30                  35

GTG CAG TCG CCC ATG TTT GAT GGA AAA GTC CCA CAC TGG TAC CAC TTC      257
Val Gln Ser Pro Met Phe Asp Gly Lys Val Pro His Trp Tyr His Phe
    40                  45                  50

TCC TGC TTC TGG AAG GTG GGC CAC TCC ATC CGG CAC CCT GAC GTT GAG      305
Ser Cys Phe Trp Lys Val Gly His Ser Ile Arg His Pro Asp Val Glu
55                  60                  65                  70

GTG GAT GGG TTC TCT GAG CTT CGG TGG GAT GAC CAG CAG AAA GTC AAG      353
Val Asp Gly Phe Ser Glu Leu Arg Trp Asp Asp Gln Gln Lys Val Lys
                75                  80                  85

AAG ACA GCG GAA GCT GGA GGA GTG ACA GGC AAA GGC CAG GAT GGA ATT      401
Lys Thr Ala Glu Ala Gly Gly Val Thr Gly Lys Gly Gln Asp Gly Ile
            90                  95                  100

GGT AGC AAG GCA GAG AAG ACT CTG GGT GAC TTT GCA GCA GAG TAT GCC      449
Gly Ser Lys Ala Glu Lys Thr Leu Gly Asp Phe Ala Ala Glu Tyr Ala
        105                 110                 115

AAG TCC AAC AGA AGT ACG TGC AAG GGG TGT ATG GAG AAG ATA GAA AAG      497
Lys Ser Asn Arg Ser Thr Cys Lys Gly Cys Met Glu Lys Ile Glu Lys
    120                 125                 130

GGC CAG GTG CGC CTG TCC AAG AAG ATG GTG GAC CCG GAG AAG CCA CAG      545
Gly Gln Val Arg Leu Ser Lys Lys Met Val Asp Pro Glu Lys Pro Gln
135                 140                 145                 150

CTA GGC ATG ATT GAC CGC TGG TAC CAT CCA GGC TGC TTT GTC AAG AAC      593
Leu Gly Met Ile Asp Arg Trp Tyr His Pro Gly Cys Phe Val Lys Asn
                155                 160                 165

AGG GAG GAG CTG GGT TTC CGG CCC GAG TAC AGT GCG AGT CAG CTC AAG      641
Arg Glu Glu Leu Gly Phe Arg Pro Glu Tyr Ser Ala Ser Gln Leu Lys
            170                 175                 180

GGC TTC AGC CTC CTT GCT ACA GAG GAT AAA GAA GCC CTG AAG AAG CAG      689
Gly Phe Ser Leu Leu Ala Thr Glu Asp Lys Glu Ala Leu Lys Lys Gln
        185                 190                 195

CTC CCA GGA GTC AAG AGT GAA GGA AAG AGA AAA GGC GAT AAG GTG GAT      737
Leu Pro Gly Val Lys Ser Glu Gly Lys Arg Lys Gly Asp Lys Val Asp
    200                 205                 210

GGA GTG GAT GAA GTG GCG AAG AAG AAA TCT AAA AAA GAA AAA GAC AAG      785
Gly Val Asp Glu Val Ala Lys Lys Lys Ser Lys Lys Glu Lys Asp Lys
215                 220                 225                 230

GAT AGT AAG CTT GAA AAA GCC CTA AAG GCT CAG AAC GAC CTG ATC TGG      833
Asp Ser Lys Leu Glu Lys Ala Leu Lys Ala Gln Asn Asp Leu Ile Trp
                235                 240                 245

AAC ATC AAG GAC GAG CTA AAG AAA GTG TGT TCA ACT AAT GAC CTG AAG      881
Asn Ile Lys Asp Glu Leu Lys Lys Val Cys Ser Thr Asn Asp Leu Lys
            250                 255                 260

GAG CTA CTC ATC TTC AAC AAG CAG CAA GTG CCT TCT GGG GAG TCG GCG      929
```

-continued

```
Glu Leu Leu Ile Phe Asn Lys Gln Gln Val Pro Ser Gly Glu Ser Ala
        265                 270                 275

ATC TTG GAC CGA GTA GCT GAT GGC ATG GTG TTC GGT GCC CTC CTT CCC      977
Ile Leu Asp Arg Val Ala Asp Gly Met Val Phe Gly Ala Leu Leu Pro
    280                 285                 290

TGC GAG GAA TGC TCG GGT CAG CTG GTC TTC AAG AGC GAT GCC TAT TAC     1025
Cys Glu Glu Cys Ser Gly Gln Leu Val Phe Lys Ser Asp Ala Tyr Tyr
295                 300                 305                 310

TGC ACT GGG GAC GTC ACT GCC TGG ACC AAG TGT ATG GTC AAG ACA CAG     1073
Cys Thr Gly Asp Val Thr Ala Trp Thr Lys Cys Met Val Lys Thr Gln
                315                 320                 325

ACA CCC AAC CGG AAG GAG TGG GTA ACC CCA AAG GAA TTC CGA GAA ATC     1121
Thr Pro Asn Arg Lys Glu Trp Val Thr Pro Lys Glu Phe Arg Glu Ile
            330                 335                 340

TCT TAC CTC AAG AAA TTG AAG GTT AAA AAG CAG GAC CGT ATA TTC CCC     1169
Ser Tyr Leu Lys Lys Leu Lys Val Lys Lys Gln Asp Arg Ile Phe Pro
        345                 350                 355

CCA GAA ACC AGC GCC TCC GTG GCC CAC CCT CCG CCC TCC ACA GCC TCG     1217
Pro Glu Thr Ser Ala Ser Val Ala His Pro Pro Pro Ser Thr Ala Ser
    360                 365                 370

GCT CCT GCT GCT GTG AAC TCC TCT GCT TCA GCA GAT AAG CCA TTA TCC     1265
Ala Pro Ala Ala Val Asn Ser Ser Ala Ser Ala Asp Lys Pro Leu Ser
375                 380                 385                 390

AAC ATG AAG ATC CTG ACT CTC GGG AAG CTG TCC CGG AAC AAG GAT GAA     1313
Asn Met Lys Ile Leu Thr Leu Gly Lys Leu Ser Arg Asn Lys Asp Glu
                395                 400                 405

GTG AAG GCC ATG ATT GAG AAA CTC GGG GGG AAG TTA ACG GGG ACG GCC     1361
Val Lys Ala Met Ile Glu Lys Leu Gly Gly Lys Leu Thr Gly Thr Ala
            410                 415                 420

AAC AAG GCT TCC CTG TGC ATC AGC ACC AAA AAG GAG GTG GAA AAG ATG     1409
Asn Lys Ala Ser Leu Cys Ile Ser Thr Lys Lys Glu Val Glu Lys Met
        425                 430                 435

AAT AAG AAG ATG GAG GAA GTA AAG GAA GCC AAC ATC CGA GTT GTG TCT     1457
Asn Lys Lys Met Glu Glu Val Lys Glu Ala Asn Ile Arg Val Val Ser
    440                 445                 450

GAG GAC TTC CTC CAG GAC GTC TCC GCC TCC ACC AAG AGC CTT CAG GAG     1505
Glu Asp Phe Leu Gln Asp Val Ser Ala Ser Thr Lys Ser Leu Gln Glu
455                 460                 465                 470

TTG TTC TTA GCG CAC ATC TTG TCC CCT TGG GGG GCA GAG GTG AAG GCA     1553
Leu Phe Leu Ala His Ile Leu Ser Pro Trp Gly Ala Glu Val Lys Ala
                475                 480                 485

GAG CCT GTT GAA GTT GTG GCC CCA AGA GGG AAG TCA GGG GCT GCG CTC     1601
Glu Pro Val Glu Val Val Ala Pro Arg Gly Lys Ser Gly Ala Ala Leu
            490                 495                 500

TCC AAA AAA AGC AAG GGC CAG GTC AAG GAG GAA GGT ATC AAC AAA TCT     1649
Ser Lys Lys Ser Lys Gly Gln Val Lys Glu Glu Gly Ile Asn Lys Ser
        505                 510                 515

GAA AAG AGA ATG AAA TTA ACT CTT AAA GGA GGA GCA GCT GTG GAT CCT     1697
Glu Lys Arg Met Lys Leu Thr Leu Lys Gly Gly Ala Ala Val Asp Pro
    520                 525                 530

GAT TCT GGA CTG GAA CAC TCT GCG CAT GTC CTG GAG AAA GGT GGG AAG     1745
Asp Ser Gly Leu Glu His Ser Ala His Val Leu Glu Lys Gly Gly Lys
535                 540                 545                 550

GTC TTC AGT GCC ACC CTT GGC CTG GTG GAC ATC GTT AAA GGA ACC AAC     1793
Val Phe Ser Ala Thr Leu Gly Leu Val Asp Ile Val Lys Gly Thr Asn
                555                 560                 565

TCC TAC TAC AAG CTG CAG CTT CTG GAG GAC GAC AAG GAA AAC AGG TAT     1841
Ser Tyr Tyr Lys Leu Gln Leu Leu Glu Asp Asp Lys Glu Asn Arg Tyr
            570                 575                 580
```

-continued

```
TGG ATA TTC AGG TCC TGG GGC CGT GTG GGT ACG GTG ATC GGT AGC AAC      1889
Trp Ile Phe Arg Ser Trp Gly Arg Val Gly Thr Val Ile Gly Ser Asn
        585                 590                 595

AAA CTG GAA CAG ATG CCG TCC AAG GAG GAT GCC ATT GAG CAC TTC ATG      1937
Lys Leu Glu Gln Met Pro Ser Lys Glu Asp Ala Ile Glu His Phe Met
    600                 605                 610

AAA TTA TAT GAA GAA AAA ACC GGG AAC GCT TGG CAC TCC AAA AAT TTC      1985
Lys Leu Tyr Glu Glu Lys Thr Gly Asn Ala Trp His Ser Lys Asn Phe
615                 620                 625                 630

ACG AAG TAT CCC AAA AAG TTC TAC CCC CTG GAG ATT GAC TAT GGC CAG      2033
Thr Lys Tyr Pro Lys Lys Phe Tyr Pro Leu Glu Ile Asp Tyr Gly Gln
            635                 640                 645

GAT GAA GAG GCA GTG AAG AAG CTG ACA GTA AAT CCT GGC ACC AAG TCC      2081
Asp Glu Glu Ala Val Lys Lys Leu Thr Val Asn Pro Gly Thr Lys Ser
            650                 655                 660

AAG CTC CCC AAG CCA GTT CAG GAC CTC ATC AAG ATG ATC TTT GAT GTG      2129
Lys Leu Pro Lys Pro Val Gln Asp Leu Ile Lys Met Ile Phe Asp Val
        665                 670                 675

GAA AGT ATG AAG AAA GCC ATG GTG GAG TAT GAG ATC GAC CTT CAG AAG      2177
Glu Ser Met Lys Lys Ala Met Val Glu Tyr Glu Ile Asp Leu Gln Lys
    680                 685                 690

ATG CCC TTG GGG AAG CTG AGC AAA AGG CAG ATC CAG GCC GCA TAC TCC      2225
Met Pro Leu Gly Lys Leu Ser Lys Arg Gln Ile Gln Ala Ala Tyr Ser
695                 700                 705                 710

ATC CTC AGT GAG GTC CAG CAG GCG GTG TCT CAG GGC AGC AGC GAC TCT      2273
Ile Leu Ser Glu Val Gln Gln Ala Val Ser Gln Gly Ser Ser Asp Ser
            715                 720                 725

CAG ATC CTG GAT CTC TCA AAT CGC TTT TAC ACC CTG ATC CCC CAC GAC      2321
Gln Ile Leu Asp Leu Ser Asn Arg Phe Tyr Thr Leu Ile Pro His Asp
            730                 735                 740

TTT GGG ATG AAG AAG CCT CCG CTC CTG AAC AAT GCA GAC AGT GTG CAG      2369
Phe Gly Met Lys Lys Pro Pro Leu Leu Asn Asn Ala Asp Ser Val Gln
        745                 750                 755

GCC AAG GTG GAA ATG CTT GAC AAC CTG CTG GAC ATC GAG GTG GCC TAC      2417
Ala Lys Val Glu Met Leu Asp Asn Leu Leu Asp Ile Glu Val Ala Tyr
    760                 765                 770

AGT CTG CTC AGG GGA GGG TCT GAT GAT AGC AGC AAG GAT CCC ATC GAT      2465
Ser Leu Leu Arg Gly Gly Ser Asp Asp Ser Ser Lys Asp Pro Ile Asp
775                 780                 785                 790

GTC AAC TAT GAG AAG CTC AAA ACT GAC ATT AAG GTG GTT GAC AGA GAT      2513
Val Asn Tyr Glu Lys Leu Lys Thr Asp Ile Lys Val Val Asp Arg Asp
            795                 800                 805

TCT GAA GAA GCC GAG ATC ATC AGG AAG TAT GTT AAG AAC ACT CAT GCA      2561
Ser Glu Glu Ala Glu Ile Ile Arg Lys Tyr Val Lys Asn Thr His Ala
            810                 815                 820

ACC ACA CAC AAT GCG TAT GAC TTG GAA GTC ATC GAT ATC TTT AAG ATA      2609
Thr Thr His Asn Ala Tyr Asp Leu Glu Val Ile Asp Ile Phe Lys Ile
        825                 830                 835

GAG CGT GAA GGC GAA TGC CAG CGT TAC AAG CCC TTT AAG CAG CTT CAT      2657
Glu Arg Glu Gly Glu Cys Gln Arg Tyr Lys Pro Phe Lys Gln Leu His
    840                 845                 850

AAC CGA AGA TTG CTG TGG CAC GGG TCC AGG ACC ACC AAC TTT GCT GGG      2705
Asn Arg Arg Leu Leu Trp His Gly Ser Arg Thr Thr Asn Phe Ala Gly
855                 860                 865                 870

ATC CTG TCC CAG GGT CTT CGG ATA GCC CCG CCT GAA GCG CCC GTG ACA      2753
Ile Leu Ser Gln Gly Leu Arg Ile Ala Pro Pro Glu Ala Pro Val Thr
            875                 880                 885

GGC TAC ATG TTT GGT AAA GGG ATC TAT TTC GCT GAC ATG GTC TCC AAG      2801
Gly Tyr Met Phe Gly Lys Gly Ile Tyr Phe Ala Asp Met Val Ser Lys
            890                 895                 900
```

-continued

```
AGT GCC AAC TAC TGC CAT ACG TCT CAG GGA GAC CCA ATA GGC TTA ATC      2849
Ser Ala Asn Tyr Cys His Thr Ser Gln Gly Asp Pro Ile Gly Leu Ile
        905                 910                 915

CTG TTG GGA GAA GTT GCC CTT GGA AAC ATG TAT GAA CTG AAG CAC GCT      2897
Leu Leu Gly Glu Val Ala Leu Gly Asn Met Tyr Glu Leu Lys His Ala
    920                 925                 930

TCA CAT ATC AGC AAG TTA CCC AAG GGC AAG CAC AGT GTC AAA GGT TTG      2945
Ser His Ile Ser Lys Leu Pro Lys Gly Lys His Ser Val Lys Gly Leu
935                 940                 945                 950

GGC AAA ACT ACC CCT GAT CCT TCA GCT AAC ATT AGT CTG GAT GGT GTA      2993
Gly Lys Thr Thr Pro Asp Pro Ser Ala Asn Ile Ser Leu Asp Gly Val
                955                 960                 965

GAC GTT CCT CTT GGG ACC GGG ATT TCA TCT GGT GTC AAT GAC ACC TCT      3041
Asp Val Pro Leu Gly Thr Gly Ile Ser Ser Gly Val Asn Asp Thr Ser
            970                 975                 980

CTA CTA TAT AAC GAG TAC ATT GTC TAT GAT ATT GCT CAG GTA AAT CTG      3089
Leu Leu Tyr Asn Glu Tyr Ile Val Tyr Asp Ile Ala Gln Val Asn Leu
        985                 990                 995

AAG TAT CTG CTG AAA CTG AAA TTC AAT TTT AAG ACC TCC CTG TGG TAATT    3139
Lys Tyr Leu Leu Lys Leu Lys Phe Asn Phe Lys Thr Ser Leu Trp
    1000                1005                1010

GGGAGAGGTA GCCGAGTCAC ACCCGGTGGC TCTGGTATGA ATTCACCCGA AGCGCTTCTG    3199

CACCAACTCA CCTGGCCGCT AAGTTGCTGA TGGGTAGTAC CTGTACTAAA CCACCTCAGA    3259

AAGGATTTTA CAGAAACGTG TTAAAGGTTT TCTCTAACTT CTCAAGTCCC TTGTTTTGTG    3319

TTGTGTCTGT GGGGAGGGGT TGTTTTGGGG TTGTTTTTGT TTTTTCTTGC CAGGTAGATA    3379

AAACTGACAT AGAGAAAAGG CTGGAGAGAG ATTCTGTTGC ATAGACTAGT CCTATGGAAA    3439

AAACCAAGCT TCGTTAGAAT GTCTGCCTTA CTGGTTTCCC CAGGGAAGGA AAAATACACT    3499

TCCACCCTTT TTTCTAAGTG TTCGTCTTTA GTTTTGATTT TGGAAAGATG TTAAGCATTT    3559

ATTTTTAGTT AAAAATAAAA ACTAATTTCA TACTATTTAG ATTTTCTTTT TTATCTTGCA    3619

CTTATTGTCC CCTTTTTAGT TTTTTTTGTT TGCCTCTTGT GGTGAGGGGT GTGGGAAGAC    3679

CAAAGGAAGG AACGCTAACA ATTTCTCATA CTTAGAAACA AAAAGAGCTT TCCTTCTCCA    3739

GGAATACTGA ACATGGGAGC TCTTGAAATA TGTAGTATTA AAAGTTGCAT TTG           3792
```

(2) INFORMATION FOR SEQ ID NO:2:

(i) SEQUENCE CHARACTERISTICS:
(A) LENGTH: 1013 amino acids
(B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:2:

```
Met Ala Glu Ser Ser Asp Lys Leu Tyr Arg Val Glu Tyr Ala Lys Ser
 1               5                  10                  15

Glu Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
```

-continued

```
65                  70                  75                  80

Asp Gln Gln Lys Val Lys Lys Thr Ala Glu Ala Gly Gly Val Thr Gly
                85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Lys Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
    290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala His Pro
        355                 360                 365

Pro Pro Ser Thr Ala Ser Ala Pro Ala Ala Val Asn Ser Ser Ala Ser
    370                 375                 380

Ala Asp Lys Pro Leu Ser Asn Met Lys Ile Leu Thr Leu Gly Lys Leu
385                 390                 395                 400

Ser Arg Asn Lys Asp Glu Val Lys Ala Met Ile Glu Lys Leu Gly Gly
                405                 410                 415

Lys Leu Thr Gly Thr Ala Asn Lys Ala Ser Leu Cys Ile Ser Thr Lys
            420                 425                 430

Lys Glu Val Glu Lys Met Asn Lys Lys Met Glu Glu Val Lys Glu Ala
        435                 440                 445

Asn Ile Arg Val Val Ser Glu Asp Phe Leu Gln Asp Val Ser Ala Ser
    450                 455                 460

Thr Lys Ser Leu Gln Glu Leu Phe Leu Ala His Ile Leu Ser Pro Trp
465                 470                 475                 480

Gly Ala Glu Val Lys Ala Glu Pro Val Glu Val Val Ala Pro Arg Gly
                485                 490                 495
```

-continued

```
Lys Ser Gly Ala Ala Leu Ser Lys Lys Ser Lys Gly Gln Val Lys Glu
            500                 505                 510

Glu Gly Ile Asn Lys Ser Glu Lys Arg Met Lys Leu Thr Leu Lys Gly
        515                 520                 525

Gly Ala Ala Val Asp Pro Asp Ser Gly Leu Glu His Ser Ala His Val
    530                 535                 540

Leu Glu Lys Gly Gly Lys Val Phe Ser Ala Thr Leu Gly Leu Val Asp
545                 550                 555                 560

Ile Val Lys Gly Thr Asn Ser Tyr Tyr Lys Leu Gln Leu Leu Glu Asp
                565                 570                 575

Asp Lys Glu Asn Arg Tyr Trp Ile Phe Arg Ser Trp Gly Arg Val Gly
            580                 585                 590

Thr Val Ile Gly Ser Asn Lys Leu Glu Gln Met Pro Ser Lys Glu Asp
        595                 600                 605

Ala Ile Glu His Phe Met Lys Leu Tyr Glu Glu Lys Thr Gly Asn Ala
    610                 615                 620

Trp His Ser Lys Asn Phe Thr Lys Tyr Pro Lys Lys Phe Tyr Pro Leu
625                 630                 635                 640

Glu Ile Asp Tyr Gly Gln Asp Glu Glu Ala Val Lys Lys Leu Thr Val
                645                 650                 655

Asn Pro Gly Thr Lys Ser Lys Leu Pro Lys Pro Val Gln Asp Leu Ile
            660                 665                 670

Lys Met Ile Phe Asp Val Glu Ser Met Lys Lys Ala Met Val Glu Tyr
        675                 680                 685

Glu Ile Asp Leu Gln Lys Met Pro Leu Gly Lys Leu Ser Lys Arg Gln
    690                 695                 700

Ile Gln Ala Ala Tyr Ser Ile Leu Ser Glu Val Gln Gln Ala Val Ser
705                 710                 715                 720

Gln Gly Ser Ser Asp Ser Gln Ile Leu Asp Leu Ser Asn Arg Phe Tyr
                725                 730                 735

Thr Leu Ile Pro His Asp Phe Gly Met Lys Lys Pro Pro Leu Leu Asn
            740                 745                 750

Asn Ala Asp Ser Val Gln Ala Lys Val Glu Met Leu Asp Asn Leu Leu
        755                 760                 765

Asp Ile Glu Val Ala Tyr Ser Leu Leu Arg Gly Gly Ser Asp Asp Ser
    770                 775                 780

Ser Lys Asp Pro Ile Asp Val Asn Tyr Glu Lys Leu Lys Thr Asp Ile
785                 790                 795                 800

Lys Val Val Asp Arg Asp Ser Glu Glu Ala Glu Ile Ile Arg Lys Tyr
                805                 810                 815

Val Lys Asn Thr His Ala Thr Thr His Asn Ala Tyr Asp Leu Glu Val
            820                 825                 830

Ile Asp Ile Phe Lys Ile Glu Arg Glu Gly Glu Cys Gln Arg Tyr Lys
        835                 840                 845

Pro Phe Lys Gln Leu His Asn Arg Arg Leu Leu Trp His Gly Ser Arg
    850                 855                 860

Thr Thr Asn Phe Ala Gly Ile Leu Ser Gln Gly Leu Arg Ile Ala Pro
865                 870                 875                 880

Pro Glu Ala Pro Val Thr Gly Tyr Met Phe Gly Lys Gly Ile Tyr Phe
                885                 890                 895

Ala Asp Met Val Ser Lys Ser Ala Asn Tyr Cys His Thr Ser Gln Gly
            900                 905                 910
```

-continued

```
Asp Pro Ile Gly Leu Ile Leu Leu Gly Glu Val Ala Leu Gly Asn Met
        915                 920                 925

Tyr Glu Leu Lys His Ala Ser His Ile Ser Lys Leu Pro Lys Gly Lys
    930                 935                 940

His Ser Val Lys Gly Leu Gly Lys Thr Thr Pro Asp Pro Ser Ala Asn
945                 950                 955                 960

Ile Ser Leu Asp Gly Val Asp Val Pro Leu Gly Thr Gly Ile Ser Ser
                965                 970                 975

Gly Val Asn Asp Thr Ser Leu Leu Tyr Asn Glu Tyr Ile Val Tyr Asp
            980                 985                 990

Ile Ala Gln Val Asn Leu Lys Tyr Leu Leu Lys Leu Lys Phe Asn Phe
        995                 1000                1005

Lys Thr Ser Leu Trp
    1010
```